United States Patent [19]

Uhr et al.

[11] Patent Number: 4,664,911
[45] Date of Patent: May 12, 1987

[54] IMMUNOTOXIN CONJUGATES EMPLOYING TOXIN B CHAIN MOIETIES

[75] Inventors: Jonathan W. Uhr; Ellen S. Vitetta, both of Dallas, Tex.

[73] Assignee: Board of Regents, University of Texas System, Austin, Tex.

[21] Appl. No.: 506,540

[22] Filed: Jun. 21, 1983

[51] Int. Cl.[4] .................. A61K 39/00; G01N 33/563; G01N 33/53; G01N 33/554
[52] U.S. Cl. ........................ 424/85; 424/88; 436/512; 436/519; 436/547; 436/813; 436/879; 530/387; 530/388
[58] Field of Search ............... 260/112 B, 112 R; 424/85, 88; 436/512, 519, 547, 813; 530/387, 388

[56] References Cited

U.S. PATENT DOCUMENTS

| | | | |
|---|---|---|---|
| 4,322,495 | 3/1982 | Kato | 424/88 X |
| 4,340,535 | 7/1982 | Voisin | 260/112 B |
| 4,356,117 | 10/1982 | Neville, Jr. et al. | 260/112 R |
| 4,359,457 | 11/1982 | Neville, Jr. | 424/85 |
| 4,368,149 | 1/1983 | Masuho | 260/112 B |
| 4,397,843 | 8/1983 | Neville, Jr. et al. | 424/177 |
| 4,414,148 | 11/1983 | Jansen | 424/85 X |
| 4,440,747 | 4/1984 | Neville, Jr. et al. | 424/85 |
| 4,500,637 | 2/1985 | Neville, Jr. | 436/824 X |

FOREIGN PATENT DOCUMENTS

| | | |
|---|---|---|
| 0023401 | 2/1981 | European Pat. Off. . |
| 0023779 | 2/1981 | European Pat. Off. . |
| 0031999 | 7/1981 | European Pat. Off. . |
| 0044167 | 1/1982 | European Pat. Off. . |
| 0055115 | 6/1982 | European Pat. Off. . |
| 0055575 | 7/1982 | European Pat. Off. . |
| 8310691 | 2/1983 | European Pat. Off. . |
| 2034324 | 6/1980 | United Kingdom . |

OTHER PUBLICATIONS

Eidels, L. et al., *Microbiol. Rev.*, vol. 47, No. 4, 1983, pp. 596–620.
Cohen, P. et al., (editor) *Molecular Action of Toxins and Viruses,* Elsevier Biomedical Press, New York, N.Y., 1984, pp. 51–105.
Roth, R. A., B. A. Maddux, K. Y. Wong, Y. Iwamoto, & I. D. Goldfine, 1981, The Journal of Biological Chemistry, vol. 256, pp. 5350–5354.
Houston, L. L., 1982, The Journal of Biological Chemistry, vol. 257, pp. 1532–1539.
Thorpe, P. E., A. N. F. Brown, W. C. J. Ross, A. J. Cumber, S. I. Detre, D. C. Edwards, A. J. S. Davies, and F. Stirpe, 1981, Eur. J. Biochem., vol. 116, pp. 447–454.
Gilliland, D. G., Z. Steplewski, R. J. Collier, K. F. Mitchell, T. H. Chang & H. Koprowski, 1980 Proc. Nat'l. Acad. Sci. USA, vol. 77, pp. 4539–4543.
Vallera, D. A., R. J. Youle, D. M. Neville, Jr., and J. H. Kersey, 1982, Journal of Experimental Medicine, vol. 155, pp. 949–954.
Olsnes, S., and A. Pihl, 1973, Biochemistry, vol. 12, pp. 3121–3126.
Thorpe et al. (1982) Immunol. Rev. V62, pp. 120–158.
Neville, Jr. (1982) Immunol. Rev. V62, pp. 75–91.
Jansen et al. (1982) Immunol. Rev. V62, pp. 185–216.
Vitetta et al. (1982) Immunol. Rev. V62, pp. 159–183.
Vitetta et al. (1983) *Proc. Natl. Acad. Sci. USA,* V 80, pp. 6332–6335.
Vitetta et al. (1984) *J. Exp. Med.,* V 160, pp. 341–346.
Krolick et al. (1982) *Nature,* V 295, pp. 604–605.
Neville, Jr. (1983), *Chem. Abs.,* p. 54, No. 98:65488Y.

*Primary Examiner*—Esther M. Kepplinger
*Assistant Examiner*—Jeremy Jay
*Attorney, Agent, or Firm*—Arnold, White & Durkee

[57] ABSTRACT

Compositions and methods for potentiating the cytotoxic activity of immunogotoxin conjugates are provided. The compositions of the present invention include a selective binding agent such as an antibody coupled to a toxin B chain moiety such as ricin B chain.

19 Claims, No Drawings

IMMUNOTOXIN CONJUGATES EMPLOYING TOXIN B CHAIN MOIETIES

BACKGROUND OF THE INVENTION

This invention relates to immunotoxin conjugates and their use to selectively delete a target population of cells. More particularly, the present invention relates to the utilization of a toxin B chain moiety coupled to a cell surface affinity binding agent to potentiate the cytotoxicity provided by a cell surface affinity binding agent coupled to a toxin A chain moiety.

Ricin is one of a number of plant proteins which, in minute quantities, exhibits considerable toxicity toward eukaryotic cells. Ricin is composed of two glycoprotein chains covalently linked via a single disulfide bond. The A chain of ricin, having an apparent molecular weight (AMW) of about 30,000, is responsible for the expression of toxicity, and acts enzymatically upon the 60S ribosomal subunit leading to irreversible abrogation of protein synthesis [Olsnes, et al., *FEBS Lett* 28, 48-50 (1972)]. Ricin B chain (AMW 32,000) functions as a lectin with specificity for galactose and serves to bind the toxin to the plasma membrane [see, for example, Baenziger, et al., *J. Biol. Chem.* 254, 9795-9799 (1979)]

The use of ricin, or the purified ricin A chain, in conjunction with antibodies, has been the subject of great interest as potentially useful reagents in tumor therapy. Antibody-ricin and antibody-A chain conjugates, or "immunotoxins", have been used in a number of systems with varying degrees of success [see, for example, Vitetta, et al., *Science* 219, 644-650 (1983); Thorpe, et al., *Immunol. Rev* 62, 120-158 (1982); Neville, et al., *Immunol. Rev.* 62, 75-91 (1982); and Jansen, et al., *Immunol. Rev.* 62, 185-216 (1982)].

Procedures for deleting selected populations of cells by ricin A chain-antibody conjugates are well recognized. The antibodies of choice are those which react with antigens on tumor cells or on subsets of normal lymphocytes. By deletion of the tumor cells, it is possible, for example, to reduce tumor burdens in vivo [Krolick, et al., *J. Exp. Med.* 155, 1797 (1982)] and to remove tumor cells from bone marrow for autologous marrow transplantation [Thorpe, et al., *Nature* (London) 271, 752 (1978); and Krolick, et al., *Nature* (London) 295 604 (1982)].

By deletion of normal subsets of lymphocytes, it is possible to "up" or "down" regulate the immune response. The advantage of immunotoxins is that they are highly selective in their target cell specificity and that small doses can eliminate unwanted cells. Ricin A chain-antibody conjugates have been used primarily to delete normal and neoplastic B cells, both in vivo and in vitro. Certain laboratories have also used conjugates of ricin A chain and monoclonal antibody to eliminate neoplastic cells of T cell origin and a variety of other cancerous cells.

However, ricin A chain-antibody conjugates are not active when used against certain types of tumor cells (e.g., some T cell tumors) [Neville, et al., *Immunol. Rev.* 62, 75 (1982); and Thorpe, et al., *Immunol. Rev.* 62, 119 (1982)].

In contrast, immunotoxins coupled to the whole ricin toxin are much more potent cytocidal agents. Unfortunately, the presence of the galactose binding site of ricin B in intact ricin prevents its use in vivo since its target cell specificity thereby is lost. Attempts to overcome the nonspecificity of ricin-containing immunotoxins by blocking the galactose binding site are ongoing; however, their use in vivo has to date not been described.

Others have described studies in which ricin A chain-antibody conjugates can be potentiated by the addition of free B chain to cell cultures (Neville et al., supra). It has been postulated, therefore, that the B chain of ricin plays two functional roles: (1) to facilitate entry of ricin into the cell by virtue of its galactose-binding properties, and (2) to allow the A chain to gain rapid access to the cytoplasm, perhaps by formation of a pore in the endocyticvesicle membrane.

In a recent unpublished study, applicants have discovered that injection of mice with nontoxic ricin A chain followed 4-8 hours later by injection with nontoxic ricin B chain produces ricin-induced death. This probably occurs by reformation of the intact ricin molecule in the serum or on the surface of circulating cells. It is therefore believed that the B chain plays an active role in potentiating the toxic activity of the ricin A chain.

SUMMARY OF THE INVENTION

The present invention provides compositions and a method for potentiating the cytotoxic activity of cell surface binding agent-toxin conjugates while at the same time retaining their exquisite target cell specificity. The compositions of the present invention include a selective binding agent coupled to a toxin B chain moiety.

Further, the present invention provides a composition comprising, in combination, a first conjugate which includes a selective binding agent coupled to a toxin B chain moiety together with a second conjugate which includes a cell surface binding agent coupled to a toxin A chain moiety. The selective binding agent of the first conjugate can be either a cell surface binding agent or a binding agent specific for the cell surface binding agent of the second conjugate.

In one aspect of the invention there is provided a conjugate which encompasses an antibody as the cell surface binding agent coupled to a ricin B chain moiety. Further, there is provided a composition comprising in combination a first conjugate of an antibody coupled to a ricin B chain moiety together with a second conjugate of an antibody coupled to a ricin A chain moiety.

In another aspect of the invention there is provided a method for eliminating target cells from a population of cells containing such target cells by contacting the population of cells with a first conjugate comprising affinity binding agent specific for an antigenic determinant on such target cells coupled to toxin B chain moiety and a second conjugate comprising a cell surface affinity binding agent specific to a different determinant on the same targetcell coupled to a toxin A chain moiety. The utilization of a mixture of such conjugates potentiates the selective cytotoxic activity provided by the conjugate comprising a cell surface affinity binding agent coupled to toxin A chain moiety.

DETAILED DESCRIPTION OF THE INVENTION

The invention will be described in terms of preferred embodiments which represent the best mode known to Applicants at the time of this application.

As a preferred embodiment, this invention is directed to a conjugate comprising antibody coupled to toxin B chain moiety. Further, this invention is directed to a method for eliminating target cells using, in concert, a composition comprising a first conjugate containing ricin B chain moiety and a second conjugate containing ricin A chain moiety.

Ricin is one of a number of toxin proteins which, in minute quantities, exhibits considerable toxicity toward cells. Ricin toxin is composed of two different glycoprotein chains covalently linked via a single disulfide bond. The A chain of ricin (AMW 30,000) is responsible for the expression of toxicity caused by irreversible abrogation of protein synthesis. Ricin B chain (AMW 32,000) functions as a lectin which binds to galactose containing glycoproteins or glycolipids exposed on cell surfaces. The general structure and mode of action exhibited by ricin is shared by a variety of plant toxin proteins such as abrin, modeccin, and viscumin, and bacterial toxin proteins such as cholera, *E. coli.* heat-labile, pertussis, tetanus, botulinum, pseudomonas, shigella, and diphtheria toxins.

The ricin B conjugate and the ricin A conjugate in the methods and compositions of this invention each comprise two active moieties: a binding agent and a toxin A or B chain subunit covalently joined, preferably via a coupling agent. In each composition at, one of the binding agents is represented by a molecule having binding affinity for a surface structure of a target cell. A binding agent of one toxin chain conjugate may have a binding affinity for the cell surface binding agent of the other toxin chain conjugate. Typically cell surface binding agents are, for example, hormones, growth factors, lectins, antibodies, and the like. The binding agents of choice are antibodies or fragments thereof (in particular, Fab fragments) having cell surface binding affinity. For binding agents an affinity for cell surface binding agents, antibodies or fragments thereof are preferred.

Monoclonal antibodies are preferred but not essential binding agents. Immunoglobulin fractions from serum can be used, albeit with a lesser degree of target specificity. Since the immunoglobulin fraction of an antiserum contains a multitude of antibodies directed to a wide range of divergent antigens, a practical usefulness of the compositions of this invention and the defined method for eliminating target cells dictates the need to isolate a desired collection of antibodies, each directed to a surface antigenic determinant present on the particular target cell.

An effective collection of such antibodies can be obtained by passing the immunoglobulin fraction over a column containing the respective antigen chemically coupled to a matrix. Antibody specific to the antigen will be retained on the column while unrelated immunoglobulin passes through. The retained antibody then can be collected by elution from the column using suitable eluting agents, for example, acidic buffers or chaotropic agents. It should be noted that the isolated immunoglobulin, although directed to a single antigen, is not homogeneous. It comprises antibodies directed to a variety of antigenic determinants present on the antigen molecule. As a result, the possibility exists for cross-reaction with other related antigens.

It is highly preferred, therefore, to use monoclonal antibodies in preparing the compositions of this invention since they are directed to only one of possibly many antigenic determinants present on an antigen. Monoclonal antibodies are available by recognized methodology from hybridomas derived from lymphocytes present in spleen or other organs.

Moreover, the use of monoclonal antibodies in the compositions used in the method of this invention carries the highly desirable feature of enhanced selectivity. It is highly preferred, therefore, that both the ricin B conjugate and the ricin A conjugate be comprised of a monoclonal antibody. This will ensure a high level of target specificity.

The preceding paragraphs have reference to one aspect of the present invention, the use of the same cell surface affinity binding agent for construction of both the ricin A chain conjugate and the ricin B chain conjugate. However, an even greater degree of specificity can be attained. Since a normal or tumor cell bears several different surface markers, it is possible to target the ricin A and the ricin B chains to such cells by coupling each to an antibody directed against a different determinant on the same cell. For example, in the case of a neoplastic B cell bearing both surface Ia (sIa) and surface Ig(sIg), immunotoxins against the sIa and the sIg idiotype can be prepared with the ricin B chain and ricin A chain, respectively. In the case of T cell tumors, there are now a number of monoclonal antibodies reactive with subsets of human T cells. By the use of selected combinations of antibodies, it is possible to target the ricin A and ricin B chains to specific subsets of such cells. Preferably, one antibody (coupled to ricin A chain) would define the subset, and the second (coupled to ricin B chain) would be a more general marker common to many subsets of cells. The B chain immunotoxin, directed against the more common marker, would bind also to normal cells; however, they would not be deleted. In contrast, the A chain-immunotoxin would be focused only on the tumor cell and would be potentiated by B chain-containing immunotoxin.

Another approach contemplated by the method of this invention involves first directing a tumor cell reactive antibody-ricin A chain conjugate to tumor cells in vivo. The antibody preferably is univalent and most preferably may be an antibody fragment, e.g. F(ab')-A, and, therefore, is unable to cap and modulate. After the antibody-ricin A conjugate has been injected into a cancer-bearing patient and the excess eliminated from the recipient by excretion or degradation, a ricin B chain-containing immunotoxin directed against the antibody of the ricin A conjugate is injected. Only those cells which had bound the first immunotoxin would focus the second immunotoxin on the first. Therefore, such cells would be selectively deleted. The second immunotoxin preferably is a divalent anti-antibody, such as a F(ab')$_2$-B, which would not bind to macrophages, monocytes, or other cells bearing Fc receptors. Furthermore, since the B chain-containing immunotoxin would be innocuous if nonspecifically bound to a cell which had not previously bound the first immunotoxin, the side effects of the administration of the second immunotoxin would be eliminated. In contrast, cells binding both immunotoxins would be killed.

As noted from the foregoing, the ricin B-containing composition of this invention and the ricin A-containing composition used in the method of this invention each comprises at least two separate active moieties, one of which affords binding affinity (BA) and the other of which is a ricin subunit (RS), whether ricin A (RA) or ricin B (RB). These are joined through a coupling reagent, the requirements of the resulting composition being (a) the presence of at least one of each class of moiety, and (b) the retention of the innate activity of at least one of each class of moiety.

Other toxin proteins may be similarly coupled to the binding agent component for use in accordance with the present invention. Due to the similarity in their structure and mode of action, plant or bacterial toxin proteins such as abrin, modeccin, viscumin, and cholera, *E. coli.* heat-labile, pertussis, tetanus, botulinum, pseudomonas, shigella and diphtheria toxins may be so utilized. Further, it may be advantageous to couple the A chain from, for example, abrin, to a cell surface binding moiety to form the first conjugate of the invention and the B chain from, for example, viscumin, to a selective binding agent moiety to form the second conjugate. It may also be found advantageous to utilize a plant protein toxin such as gelonin, which consists only of an A chain, as the A chain to be coupled to the cell surface binding moiety to form the first conjugate in conjunction with a conjugate comprising a selective binding moiety coupled to a B chain selected from any one of the toxins ricin, viscumin, modeccin or abrin.

In accordance with the above limitations, the compositions of this invention and those used in the method of this invention can be dimeric (BA-RS), i.e., contain one of each class of moiety; trimeric [(BA$_2$-RS) or (BA-RS$_2$)], i.e., contain two of one class of moiety and one of the other; tetrameric [(BA$_3$-RS), (BA$_2$-RS$_2$), or (BA-RS$_3$)]; and the like.

As noted, highly preferred compositions of this invention for use in the method of this invention are those in which the binding moiety is antibody or an antigen binding fragment of antibody, and preferably monoclonal antibody or an antigen binding fragment thereof. Typical such compositions are Ab-RB, Ab$_2$-RB, Ab-RB$_2$, Ab$_3$-RB, Ab$_2$-RB$_2$, Ab-RB$_3$, Ab-RA, Ab$_2$-RA, Ab-RA$_2$, Ab$_3$-RA, Ab$_2$-RA$_2$, Ab-RA$_3$, and the like.

In preparing the compositions of this invention, the BA and RS moieties are joined via a suitable coupling reagent. A wide variety of coupling agents is reported in Ghose, T., and Blair, A. H., *J. Natl. Cancer Inst.* 61, 657–676 (1980). This paper reports, in coupling antibody to cytotoxic agents, the use of carbodiimides as well as other bifunctional reagents, such as glutaraldehyde, p-benzoquinone, p,p'-difluoro-m,m'dinitrodiphenylsulfone, dimethyl adipimidate, and the like. Since it is highly desirable to preclude formation of homopolymers, e.g., (BA)$_n$ or (RS)$_n$, it is preferred to use a heterobifunctional reagent, thereby ensuring formation of compositions having at least one of each class of moiety, i.e., those defined by this invention, with prevention of the formation, even in part, of homopolymers. Examples of such heterobifunctional reagents are N-succinimidyl-3-(2-pyridyldithio)propionate (SPDP), m-maleimidobenzoyl-N-hydroxy-succinimidyl ester, bromoacetyl-p-aminobenzoyl-N-hydroxy-succinimidyl ester, iodoacetyl-N-hydroxysuccinimidyl ester, and the like.

As an example, using SPDP as coupling agent, a composition of this invention containing Ab and RS can be prepared by (a) separately modifying both Ab and RS by reaction with SPDP, (b) reducing the Ab-containing product, (c) causing formation of the composition by mixing the Ab-containing and RS-containing products, and (d) separating non-reacted monomers by gel filtration.

The conjugates of this invention containing ricin B, when used in concert with ricin A conjugates in accordance with the method of this invention, have general applicability in the specific and selective killing of a cell type defined by particular antigenic markers. By appropriate selection of the antigenic marker the cell surface binding agent can be directed to either a set of normal cells or to a subset of neoplastic cells bearing a distinguishing determinant. As such, they are useful, for example, in the immunotherapy of cancer, for treating parasitic infections, and for treating a wide range of autoimmune diseases. Moreover, the compositions have several in vitro applications, including, for example, elimination of leukemic cells in bone marrow prior to autologous bone marrow transplantation; elimination of T cells in bone marrow prior to allogeneic bone marrow transplantation; and killing of wild types for selection of mutants.

The compositions of this invention as well as those used in the method of this invention can be used in a variety of pharmaceutical formulations and can be administered by a variety of conventional routes, such as intramuscular, intravenous, subcutaneous, and intraperitoneal.

In administering the compositions defined by this invention parenterally or intraperitoneally, the pharmaceutical forms suitable for injection include sterile aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compositions defined by this invention in the required amount of the appropriate solvent with various of the other ingredients, as desired.

If desired, and for more effective distribution, the compositions can be incorporated into slow release systems such as polymer matrices, liposomes, and microspheres. Moreover, the compositions can be administered either alone or as a mixture of a plurality of active ingredients.

Doses of the compositions are administered to the recipient for a period during which a therapeutic response is desired. The weight of the recipient and mode of administration will have an influence upon the size of the dose necessary to induce a particular response.

It is especially advantageous to formulate the compositions defined by this invention in unit dosage form for ease of administration and uniformity of dosage. Unit dosage form as used herein refers to a physically discrete unit suited as unitary dosages for the subject to be treated. Each unit contains a predetermined quantity of the composition calculated to produce the desired therapeutic effect in association with the pharmaceutically acceptable carrier. The specific unit dosage form is dictated by and directly dependent upon (a) the unique characteristics of the particular composition and (b) the particular therapeutic effect to be achieved.

The following examples are illustrative of this invention. They are not intended to be limiting upon the scope thereof.

I. PREPARATION OF IMMUNOTOXINS

A. RICIN A AND B CHAIN

The A and B chain subunits of ricin were each purchased from Xoma Corporation, San Francisco, Calif. Prior to use, the A and B chains were extensively dialyzed at 4° C. against phosphate buffered saline (PBS) pH 7.2. The recovery of the A and B chains were 50% and 80%, respectively.

B. ANTIBODY

The selective and cell surface binding agent of this embodiment is affinity purified rabbit anti-human immunoglobulin (RaHIg) made according to protocol generally described in the literature.

C. CONJUGATION

10 μl of 60 mM dithiothreitol (DTT) in PBS was added to each mg of the dialyzed A or B chain. The mixtures were incubated at 25° C. for 60 minutes and the reduced chains were separated from the DTT by gel filtration at 25° C. on a Sephadex G-25 column (18×1.5 cm) in PBS pH 7.2. Antibodies were coupled as described previously in Vitetta, et al., *Immunol. Rev.* 62:159–183 (1982) and were mixed with the freshly reduced A or B chains at an antibody:A chain or antibody:B chain molar ratio of 5:1. The mixture was incubated for 15 minutes at 4° C. with gentle shaking and then dialyzed overnight against PBS at 4° C. The immunotoxins were concentrated to 1 mg/ml by pervaporation, dialyzed for 2–16 hours at 4° C. against PBS, and centrifuged to remove insoluble material. The separation of the immunotoxin from the majority of free A chain, B chains and antibody was performed by gel filtration at 25° C. on a Sephacryl-S200 column equilibrated with PBS, pH 7.2. Material with an apparent molecular weight of greater than 200,000 was pooled. Reduced and alkylated bovine alpha globulin, fraction 4 (Sigma) was added to a final concentration of 1 mg/ml to the pooled samples. The samples were stored 16–20 hours at 4° C. prior to affinity purification.

The RaHIg-A chain (RaHIg-A) and RaHIg-B chain (RaHIg-B) immunotoxins were affinity purified on Sepharose-HIg. For purification of the A chain-containing immunotoxins, the columns were equilibrated and washed in PBS, pH 7.2 and for the affinity purification of the B chain-containing immunotoxins, the columns were equilibrated and washed in PBS, pH 7.6 containing 0.1M galactose. Samples were applied to the column and the fall-through was discarded. The columns were extensively washed in PBS (or PBS-0.1M gal) followed by 0.85% NaCl. Immunotoxins were eluted batch-wise at 37° C. with 2–3 column volumes of 3.5M $MgCl_2$. The $MgCl_2$ was removed by dialysis and the samples were concentrated by pervaporation to approximately 200–300 ug/ml. Reduced and alkylated bovine alpha globulin was added to a final concentration of 1 mg/ml. Samples were sterilized by filtration [on a filter prewetted with PBS 2% fetal calf serum (FCS)], and then aliquoted into sterile vials and stored at −20° C. Samples stored in this manner were stable for up to 4–6 months.

The recovery of the immunotoxin following affinity purification was 26–45% and each immunotoxin contained one or two A (or B) chain subunits per molecule of antibody. When immunotoxins were analyzed on SDS-PAGE slab gels using a sensitive silver staining technique, there was no detection of free A or B chains in any of the immunotoxins.

II. USE OF RICIN B CHAIN CONTAINING CONJUGATES AND RICIN A CHAIN CONJUGATES IN THE KILLING OF NEOPLASTIC HUMAN B CELLS

A. NEOPLASTIC CELL CULTURE

The human Burkitt's lymphoma cell line, Daudi, as described in Houston, L. L., *Biochem. Biophys. Res. Commun.* 92:319–326 (1980), was maintained in suspension culture in RPMI-1640 supplemented with 10% (v/v) fetal calf serum (FCS), 20 mM fresh glutamine, and antibiotics. Cultures were maintained at 37° C. in a humid incubator with a 95% $O_2$/5% $CO_2$ atmosphere. All cultures were utilized two days following subculture.

B. TREATMENT OF DAUDI CELLS

Two days after subculture, Daudi cells were harvested and washed in buffered saline solution (BSS). $10^5$ cells in BSS were distributed into microtiter wells. Dilutions of each of the two immunotoxins, RaHIg-A and RaHIg-B, or combination of both, were added to triplicate wells for 15 minutes at 4° C. Cells were centrifuged and washed three times in BSS. 200 ul of RPMI lacking leucine and containing 10% FCS were added to each well and the cells were resuspended by gentle agitation. Plates were cultured for 22 hours at 37° in a 5% $CO_2$ incubator. Cells were then pulsed for 6 hours at 37° in 5% $CO_2$ with 5 uCi per well of $^3$H-leucine (New England Nuclear). Cells were harvested onto glass fiber discs and counted in a liquid scintillation spectrometer. Cells were treated with each of the immunotoxins individually as well as the following combinations of immunotoxins:

1. A nontoxic amount of RaHIg-A (0.3 μg/ml) plus different amounts of RaHIg-B, or
2. A nontoxic amount of RaHIg-B (0.5 ug/ml) followed by different amounts of RaHIg-A.

The results are tabulated in the following TABLE.

TABLE

| CONCENTRATION | % of cells remaining after treatment vs. control | | | |
|---|---|---|---|---|
| ug/ml | ITB* | ITA** | ITA + ITB (0.5 ug/ml) | ITB + ITA (0.3 ug/ml) |
| 2.6 | 82 | 18 | 5 | 10 |
| 1.3 | 90 | 22 | 6 | 20 |
| 0.5 | 100 | | | |
| 0.3 | 100 | 82 | 12 | 50 |
| 0.05 | 90 | 90 | 40 | 64 |
| 0.03 | 83 | 100 | 75 | 95 |

*ITB = immunotoxin B conjugate (RaHIg-B)
**ITA = immunotoxin A conjugate (RaHIg-A)

As featured in the TABLE, when Daudi cells were treated with 0.3 μg of RaHIg-A chain/$10^5$ cells, little toxicity was observed. No concentration of RaHIg-B was toxic. However, when 0.3 ug of the RaHIg-A was mixed with various combinations of RaHIg-B, there was significant cytoxicity. It should be noted that this treatment of the Daudi cells with the mixture of immunotoxins was performed in BSS lacking galactose. As shown in the TABLE, when Daudi cells were treated with 0.5 μg of RaHIg-B, no toxicity was observed. In contrast, the RaHIg-A killed the Daudi cells in a dose-related manner. However, treatment of cells with 0.5 ug of RaHIg-B mixed with RaHIg-A was toxic to the cells, even at those concentrations at which RaHIg-A itself was no longer toxic.

While the compositions and methods of this invention have been described in terms of preferred embodiments, it will be apparent to those of skill in the art that various changes may be made in the methods and compositions disclosed without departing from the scope of the invention, which is defined by the following claims.

What is claimed is:

1. A cytotoxic composition comprising, in combination:
   a first conjugate comprising a specific binding agent covalently coupled to toxin A chain or toxin B chain moiety, together with
   a second conjugate comprising a binding agent having an affinity for a cell surface structure of a target cell or for the binding agent of the first conjugate, said binding agent being covalently coupled to toxin A chain or toxin B chain moiety, the first conjugate and second conjugate each having a different toxin chain.

2. The composition according to claim 1 wherein at least one binding agent has an affinity for a target cell surface antigenic determinant.

3. The composition according to claim 1 wherein each binding agent is a F(ab') antibody fragment.

4. The composition according to claim 1 wherein the toxin A chain and toxin B chain are the respective A and B chain moieties derived from the toxins ricin, abrin, modeccin, viscumin, cholera, *E. coli* heat-labile, pertussis, tetanus, botulinum, Pseudomonas, shigella or diphtheria.

5. The composition according to claim 1 wherein the toxin A chain moiety is ricin A chain and wherein the toxin B chain moiety is ricin B chain.

6. The composition according to claim 1 wherein each binding agent is an antibody.

7. The composition according to claim 6 wherein each of the first and second conjugates comprises an antibody having identical specificity to a cell surface antigenic determinant.

8. The composition according to claim 6 wherein the first conjugate comprises a first antibody having specificity for a cell surface antigenic determinant and the second conjugate comprises a a second antibody having a binding affinity for a target cell surface antigenic determinant different from that of the first antibody.

9. The composition according to claim 6 wherein each antibody has binding affinity for a specific tumor cell antigen.

10. The composition according to claim 6 wherein the second conjugate comprises an antibody having specificity for a cell surface antigenic determinant and the first conjugate comprises an antibody having specificity for the antibody of the second conjugate.

11. A method for potentiating the cytotoxicity of toxin A chain containing conjugates effective to selectively delete target cells from a population of cells, the method comprising:
    contacting the population of cells with a first conjugate comprising
    a binding agent having an affinity for an antigenic determinate of the target cell surface, the binding agent being covalently coupled to a toxin A chain, and
    a second conjugate comprising
    a binding agent having affinity for an antigenic determinant of the targe cell surface or for an antigenic determinant of the binding agent of the first conjugate, the binding agent being covalently coupled to toxin B chain,
    the amount of the combination of the first conjugate and the second conjugate being an amount effective to selectively delete a significant portion of target cells from a population of cells.

12. The method according to claim 11 wherein the target cells comprise tumor cells.

13. The method according to claim 11 wherein at least one binding agent is a F(ab') antibody fragment.

14. The method according to claim 11 wherein the toxin A chain moiety and toxin B chain moiety are the respective A and B chain moieties derived from the toxins ricin, abrin, modeccin, viscumin, cholera, *E. coli* heat-labile, pertussis, tetanus, botulinum, Pseudomonas, shigella or diphtheria.

15. The method according to claim 11 wherein the toxin A chain moiety is ricin A chain and the toxin B chain moiety is ricin B chain.

16. The method according to claim 11 wherein each of the binding agents of the first and second conjugates is an antibody.

17. The method according to claim 16 wherein each of the first and second conjugates comprise antibody having identical specificity for a target cell surface antigenic determinant.

18. The method according to claim 16 wherein the antibody has specificity for a cell surface antigenic determinant of a tumor cell.

19. The method according to claim 16 wherein the binding agent of the first conjugate is a first antibody having affinity for a cell surface antigenic determinant of the target cells and the binding agent of the second conjugate is a second antibody having specific affinity for a cell surface antigenic determinant of the target cells different from the first antibody.

* * * * *